(12) United States Patent
Bauer et al.

(10) Patent No.: US 9,074,510 B2
(45) Date of Patent: Jul. 7, 2015

(54) REDUCING AGENT TANK HAVING A SENSOR FOR DETERMINING A FILL LEVEL AND MOTOR VEHICLE HAVING THE TANK

(75) Inventors: Peter Bauer, Siegburg (DE); Jan Hodgson, Troisdorf (DE)

(73) Assignee: EMITEC Gesellschaft fuer Emissionstechnologie mbH, Lohmar (DE)

( * ) Notice: Subject to any disclaimer, the term of this patent is extended or adjusted under 35 U.S.C. 154(b) by 0 days.

(21) Appl. No.: 13/609,601

(22) Filed: Sep. 11, 2012

(65) Prior Publication Data

US 2014/0096512 A1 Apr. 10, 2014

Related U.S. Application Data

(63) Continuation of application No. PCT/EP2011/053493, filed on Mar. 8, 2011.

(30) Foreign Application Priority Data

Mar. 11, 2010 (DE) .......................... 10 2010 011 151

(51) Int. Cl.
   *F01N 3/01* (2006.01)
   *F01N 3/20* (2006.01)
   (Continued)

(52) U.S. Cl.
   CPC .............. *F01N 3/208* (2013.01); *F01N 3/2066* (2013.01); *F01N 13/008* (2013.01);
   (Continued)

(58) Field of Classification Search
   CPC ..... F02D 41/029; F01N 9/002; F01N 3/0842; F01N 3/035; F01N 13/02

USPC .............. 60/295, 301; 73/304 C, 292, 304 R; 174/17 R, 17 LF, 50, 70 S, 68.1, 520, 174/480, 47
See application file for complete search history.

(56) References Cited

U.S. PATENT DOCUMENTS 4,467,646 A * 8/1984 Berryman et al. .......... 73/304 C
6,994,589 B2 2/2006 Schliese
(Continued)

FOREIGN PATENT DOCUMENTS

DE 19743302 C1 2/1999
DE 198 42 484 A1 12/1999
(Continued)

OTHER PUBLICATIONS

Machine Translation of JP 2008-082201, Translated on Jul. 18, 2014.*
(Continued)

*Primary Examiner* — Thomas Denion
*Assistant Examiner* — Patrick Maines
(74) *Attorney, Agent, or Firm* — Laurence A. Greenberg; Werner H. Stemer; Ralph E. Locher (57) ABSTRACT

A tank for a reducing agent includes a tank wall having an outer side and an interior at least partially delimited by the tank wall. A sensor is disposed at the tank wall and has a first electrical contact and a second electrical contact. The first electrical contact and the second electrical contact communicate in an electrically conductive manner with the interior, extend through the tank wall from the interior to the outer side of the tank wall and are disposed at a first spacing of less than 5 cm from one another. A motor vehicle having the tank is also provided.

10 Claims, 3 Drawing Sheets

(51) Int. Cl.
*F01N 13/00* (2010.01)
*G01F 23/24* (2006.01)
*F24H 9/20* (2006.01)
*G01N 27/02* (2006.01)
*B01D 35/027* (2006.01)

(52) U.S. Cl.
CPC .... *F01N 2610/10* (2013.01); *F01N 2610/1406* (2013.01); *F01N 2900/1806* (2013.01); *G01F 23/242* (2013.01); *Y02T 10/24* (2013.01); *F01N 3/20* (2013.01); *F24H 9/2007* (2013.01); *G01N 27/02* (2013.01); *B01D 35/027* (2013.01)

(56) References Cited

U.S. PATENT DOCUMENTS

| | | | |
|---|---|---|---|
| 7,647,767 | B2 | 1/2010 | Osaku |
| 7,776,265 | B2 | 8/2010 | Berryhill et al. |
| 7,912,360 | B2 | 3/2011 | Gschwind |
| 8,746,030 | B2 | 6/2014 | Kasahara |
| 2004/0093943 | A1* | 5/2004 | Arias ............ 73/304 C |
| 2006/0103393 | A1 | 5/2006 | Stahlmann et al. |
| 2006/0145707 | A1* | 7/2006 | Ooe ............... 324/661 |
| 2010/0236243 | A1 | 9/2010 | Lolas et al. |
| 2011/0011178 | A1* | 1/2011 | Ulrich et al. ........ 73/292 |
| 2011/0155262 | A1* | 6/2011 | Ante et al. ......... 137/341 |
| 2011/0210836 | A1 | 9/2011 | Baumeister |
| 2011/0309087 | A1* | 12/2011 | Hodgson et al. ..... 220/562 |
| 2012/0111870 | A1* | 5/2012 | Hodgson et al. ..... 220/562 |
| 2012/0311999 | A1* | 12/2012 | Hodgson et al. ...... 60/295 |

FOREIGN PATENT DOCUMENTS

| | | | |
|---|---|---|---|
| DE | 198 41 770 | A1 | 4/2000 |
| DE | 19841770 | A1 * | 4/2000 ............ G01F 23/24 |
| DE | 10047594 | A1 | 4/2002 |
| DE | 10128301 | A1 | 1/2003 |
| DE | 202006010615 | U1 | 10/2006 |
| DE | 102008031645 | A1 | 1/2010 |
| DE | 102008056860 | A1 | 5/2010 |
| DE | 102009009711 | A1 | 8/2010 |
| DE | 102009001736 | A1 | 9/2010 |
| DE | 102009030674 | A1 | 12/2010 |
| EP | 1662103 | A1 | 5/2006 |
| JP | S5886528 | U | 6/1983 |
| JP | S6174836 | U | 5/1986 |
| JP | 2004212342 | A | 7/2004 |
| JP | 2005264933 | A | 9/2005 |
| JP | 2007047006 | A | 2/2007 |
| JP | 2008082201 | A * | 4/2008 |
| JP | 2009025168 | A | 2/2009 |
| JP | 2009144644 | A | 7/2009 |
| JP | 2009228616 | A | 10/2009 |
| JP | 2010007568 | A | 1/2010 |
| JP | 2010024896 | A | 2/2010 |
| JP | 2010048772 | A | 3/2010 |
| WO | 02/27280 | A2 | 4/2002 |
| WO | WO 0227280 | A2 * | 4/2002 |
| WO | 2010000827 | A1 | 1/2010 |

OTHER PUBLICATIONS

Machine Translation of DE 19841770 A1, Translated on Jul. 18, 2014.*
International Search Report of PCT/EP2011/053493, Dated May 13, 2011.

* cited by examiner

REDUCING AGENT TANK HAVING A SENSOR FOR DETERMINING A FILL LEVEL AND MOTOR VEHICLE HAVING THE TANK

CROSS-REFERENCE TO RELATED APPLICATION

This is a continuation, under 35 U.S.C. §120, of copending International Application No. PCT/EP2011/053493, filed Mar. 8, 2011, which designated the United States; this application also claims the priority, under 35 U.S.C. §119, of German Patent Application DE 10 2010 011 151.1, filed Mar. 11, 2010; the prior applications are herewith incorporated by reference in their entirety.

BACKGROUND OF THE INVENTION

Field of the Invention

The invention relates to a tank, in particular a tank for a liquid urea-water solution in a mobile application, having a sensor for determining a fill level in the tank. The invention also relates to a motor vehicle having the tank.

Exhaust-gas purification devices, into which a reducing agent is supplied for the reduction of certain exhaust-gas constituents, are known, in particular for mobile internal combustion engines in motor vehicles. It is, for example, possible for nitrogen oxide compounds (NOx) in the exhaust gas to be eliminated in a particularly effective manner if ammonia is supplied as reducing agent to the exhaust gas. Typical reducing agents such as, for example, ammonia are hazardous substances and therefore should not be stored in motor vehicles directly. Therefore, reducing agent is generally stored in the form of a reducing agent precursor in a separate tank as an additional operating fluid in the motor vehicle. A typical reducing agent precursor is, for example, urea. Urea is stored in the motor vehicle, for example, in the form of a 32.5% urea-water solution. A urea-water solution of that type is available, for example, under the trademark "AdBlue".

A urea-water solution of that type typically freezes at temperatures of −11° C. A device for delivering and/or dosing liquid reducing agent is then no longer capable of delivering the urea-water solution. Such low temperatures may occur in motor vehicles, in particular as a result of long standstill periods. It is desirable to be able to reliably determine whether liquid or frozen reducing agent is present in a tank for reducing agent. Merely for the sake of completeness, it is pointed out at this juncture that the expression "reducing agent" should also be understood to include reducing agent precursors (such as, in particular, aqueous urea).

Furthermore, the consumption of reducing agent is generally low. The consumption of reducing agent is typically approximately 0.5% to 10% of the fuel consumption of an internal combustion engine. It is therefore sought to provide a simple and inexpensive sensor configuration for fill level determination. A complex continuous fill level determining method is generally not required. At the same time, however, high demands are placed, in particular, on the determination of a reserve fill level, so as to always ensure the desired purification action of the exhaust-gas treatment system.

SUMMARY OF THE INVENTION

It is accordingly an object of the invention to provide a reducing agent tank having a particularly advantageous sensor for determining a fill level and a motor vehicle having the tank, which overcome the hereinafore-mentioned disadvantages and at least partially solve the highlighted technical problems of the heretofore-known tanks and vehicles of this general type.

With the foregoing and other objects in view there is provided, in accordance with the invention, a tank for a reducing agent. The tank comprises a tank wall having an outer side, an interior at least partially delimited by the tank wall, and a sensor disposed at the tank wall and having a first electrical contact and a second electrical contact. The first electrical contact and the second electrical contact communicate in an electrically conductive manner with the interior, extend through the tank wall from the interior to the outer side of the tank wall and are disposed at a first spacing of less than 5 cm from one another.

The first electrical contact and the second electrical contact are preferably disposed at a first spacing of less than 3 cm, particularly preferably even less than 2 cm, from one another. The feature according to which the first electrical contact and the second electrical contact extend through the tank wall is intended to mean, in particular, that the first electrical contact and the second electrical contact produce an electrical connection from the interior of the tank to an outer side of the tank.

In accordance with another feature of the invention, at least the first electrical contact and/or the second electrical contact may be formed by a metallic pot which is disposed in the tank. Such a pot may, for example, be a housing for a dosing device which is provided for delivering reducing agent out of the tank. At least the first electrical contact and/or the second electrical contact may furthermore be formed with an extraction line, a return line, an extraction point or an outlet line for the dosing device. An extraction line, a return line, an extraction point and an outlet line are various lines through which the dosing device for delivering the reducing agent is connected to the interior of the tank. It is necessary, for the functioning of the tank, for the first electrical contact to be electrically insulated with respect to the second electrical contact in order to ensure that electrical properties of the reducing agent in the tank can be determined.

In accordance with a further advantageous feature of the invention, one electrical contact is formed by a metallic pot and the other electrical contact extends through the metallic pot. Further explanations in this regard are given, in particular, in conjunction with FIG. 9.

In accordance with an added likewise advantageous feature of the invention, one electrical contact is formed with a metallic pot, the metallic pot is surrounded by a filter and the other electrical contact is disposed outside the filter. Further explanations in this regard are given, in particular, in conjunction with FIG. 10.

The tank wall is preferably produced from plastic. The electrical contacts which together form the sensor are preferably cast into the tank wall. It is additionally possible, if appropriate, for at least one sealing element to be jointly cast into the tank wall. The sealing element seals off the electrical contacts with respect to the tank wall. The electrical contacts are preferably in the form of metallic pins. The metallic pins may, if appropriate, have a surface structure which promotes the sealing of the tank wall against the metallic pins. It is also possible, if appropriate, for a groove to be formed into the metallic pins. A sealing element such as, for example, an O-ring seal, engages into the groove. If appropriate, the metallic pins may also have a bulged portion through which improved sealing of the pins in the tank wall is attained.

It is possible firstly for the electrical contacts to extend in each case individually through the tank wall. It is, however, also possible for the metallic pins to be disposed in a common sealing element and for the sealing element as a whole to be embedded into the tank wall or extend through the tank wall.

It is basically possible for a plurality of such sensors to be provided, but it is preferable for only a single sensor to be provided on a tank of this type. A plurality of such sensors may be provided in a tank, for example, in order to be able to carry out a measurement reliably at least at one of the sensors in the case of low fill levels and/or when the tank is in an oblique position. In the case of low fill levels, an oblique position of the tank may have the result that no reducing agent is present at a sensor even though reducing agent would actually still be present at the sensor, in the case of a certain reducing agent quantity stored in the tank, if the tank were in a horizontal alignment. The error rate of the fill level measurement system can consequently be reduced in this way.

Where "electrical contacts" are referred to herein, this means the first electrical contact and the second electrical contact and this terminology is not intended to express that the first electrical contact and the second electrical contact must then always have identical construction. In fact, this is intended to express that at least one of the contacts may be constructed in this way. This applies correspondingly to other generalizations, for example to pins, seals, etc.

In accordance with an additional particularly preferred feature of the invention, the sensor is disposed on a tank base. A fill level in the tank can be determined through the use of the sensor explained above. In particular, it is possible to determine a reserve fill level because a discrete fill level determination is possible through the use of a measurement between the two electrical contacts. For this purpose, a voltage is applied to the electrical contacts and an electrical resistance (or a conductance value=reciprocal of the resistance) between the electrical contacts is determined. It can be inferred, as a function of the measurement value, whether and/or how much reducing agent is present in the first spacing between the two electrical contacts of the sensor and/or what state of aggregation (for example liquid or frozen) the reducing agent is in.

The reserve fill level in the tank is determined preferably in the vicinity of the tank base because in the vicinity of the tank base, the two electrical contacts may be disposed at the same level. Furthermore, a configuration in the vicinity of the tank base permits a particularly advantageous determination of a residual volume. Specifically, a residual volume generally constitutes only an areal coverage of the tank base. Additionally, a sensor disposed in the tank base may be disposed in the center of the tank base. In this way, the sensor is made less sensitive to sloshing movements in the tank and/or to a possible oblique position of the tank, because sloshing movements and/or an oblique position cause a (particularly pronounced) change in the fill level specifically at a distance from the center, at the edge close to the tank side walls. Furthermore, tanks in motor vehicles are, if appropriate, installed so as to allow access to the tank only from below. The sensor is therefore particularly easily accessible, for example, for maintenance work if it is disposed in the tank base.

In accordance with yet another particularly preferable feature of the invention, the electrical contacts project from the tank base into the tank interior with a first length of at most 5 cm [centimeters], preferably between 0.2 cm and 2 cm, particularly preferably between 0.5 cm and 1 cm. In the region of the first length, the electrical contacts are preferably blank, that is to say, in particular, not electrically insulated. Consequently, an electrical current can pass from the electrical contacts into the reducing agent over the entirety of the first length.

In a further advantageous embodiment, the sensor may also be disposed on a tank wall. It is, in particular, also possible for a plurality of sensors, for example between two sensors and ten sensors, to be distributed over a periphery of the tank at a certain level. It is thus possible, through the use of the multiplicity of sensors, to perform monitoring of the tank, since even in the case of an oblique position and in the event of sloshing movements in the tank, at least one of the sensors is suitable for a representative measurement.

The fill level signals determined by the individual sensors may be evaluated in a suitable controller in order to obtain a corrected fill level signal. For example, a mean value may be formed from the individual fill level signals in order to determine whether or not a reserve level to be monitored has been undershot. In a further structural variant, a decision as to whether or not a reserve level has been undershot may also be made by determining the ratio of the number of sensors at which reducing agent is present to the total number of sensors provided. If, for example, more than half of the sensors signal that the reserve level has been undershot, it can be decided that the reserve level has been undershot. A statistical evaluation of the fill level signals of the plurality of sensors, for example through the use of principal component analysis, is also possible.

In a further advantageous embodiment, a shoulder with a reserve height is disposed in the region of the electrical contacts. The shoulder insulates the electrical contacts up to the reserve level. In this way, in the case of electrical contacts disposed in the tank base, a reserve level fill quantity is precisely defined.

In accordance with yet a further advantageous feature of the invention, the tank has a heater and the heater is disposed at a spacing of less than 50 cm [centimeters] from the sensor. The second spacing is preferably less than 20 cm and particularly preferably less than 10 cm. For this purpose, the heater is disposed, in particular, in the vicinity of the tank base. The heater is, in particular, a regulable electric heater (for example having at least one element from the group including heating wire, heating foil, PTC element, cooling water heating configuration). In the case of a cooling water heating configuration, it is preferable for a heating coil to be guided through the tank. The cooling water heated by the internal combustion engine flows through the heating coil and dissipates heat energy to the reducing agent in the tank.

If the reducing agent in the tank has completely frozen, a cavity in the frozen reducing agent (a so-called "ice cavity") forms in the vicinity of the tank base during the operation of a heater and (partially) liquid reducing agent is present in the cavity. The size of the ice cavity can be determined through the use of a sensor which is disposed at a defined second spacing from the heater and which has two electrical contacts. Firstly, a sensor composed of two electrical contacts can determine, through the use of a conductance value measurement, whether liquid reducing agent or frozen reducing agent is present at the sensor. Furthermore, it is possible to infer a temperature distribution in the tank therefrom. In order to determine temperature distribution in the tank, it is additionally possible to take into consideration the energy introduced into the tank by the heater.

In accordance with yet an added feature of the invention, a temperature sensor is attached at least to one electrical contact on the outer side of the tank wall. Electrically conductive contacts generally have good thermal conductivity due to their inherent electrical conductivity. By contrast, the tank wall, which is preferably produced from plastic, has poor thermal conductivity. The electrical contacts thus constitute a thermal bridge through the tank wall. This can be utilized to attach a temperature sensor to the outside of a tank wall, and to determine a temperature on the inner side of the tank wall or in the interior of the tank through the use of the temperature sensor and one of the two electrical contacts. The possibilities for determining a temperature distribution in the tank are further improved through the use of a sensor of this type.

An advantageous method for operating a tank which has a sensor with a first electrical contact and a second electrical contact will also be proposed below. The method includes at least the following steps:

a.1) defining a conductance value for liquid reducing agent;
a.2) defining a conductance value for frozen reducing agent;
a.3) defining a conductance value for air;
b) applying a voltage between the first electrical contact and the second electrical contact;
c) detecting a conductance value between the first electrical contact and the second electrical contact; and
d) comparing the conductance value detected in step c) with the conductance values defined in steps a.1) to a.3) and determining whether liquid reducing agent, frozen reducing agent or air is present.

It is firstly pointed out in this case that electrical variables are referred to herein at all times (conductance value, voltage, contact, resistance . . . ). Furthermore, it should be noted that steps a.1), a.2) and/or a.3) need not be carried out every time a determination of the fill level and/or of the state of aggregation is performed, but rather if appropriate need be carried out only once. The corresponding conductance values may then be stored (permanently) as guide values or as a tolerance range and taken into consideration as a reference in step d) for the conductance values presently measured in step c). Consequently, the conductance values from steps a.1), a.2) and a.3) may also be referred to as reference conductance values. The conductance values of liquid reducing agent and frozen reducing agent generally differ in such a way that, as a result of a determination of the conductance value, it can be inferred whether liquid reducing agent or frozen reducing agent is present. Air is a highly effective electrical insulator in relation to reducing agent, so that on the basis of a conductance value determination between the two electrical contacts, air can also be identified. The conductance value of frozen reducing agent and the conductance value of air are similar.

A conductance value which was measured at an earlier point in time may be used as a reference for the conductance value of liquid reducing agent. The tank should, with certainty, have stored liquid reducing agent at that point in time. A temperature sensor can be used to determine if this is the case. If a temperature above a defined threshold temperature has been measured through the use of a temperature sensor positioned on or in the tank or on or in a dosing unit for reducing agent, it can be assumed with certainty that liquid reducing agent is present in the tank.

In accordance with yet an additional feature of the invention, an integrally injection molded or integrally cast protective frame may furthermore be attached to or formed as one piece with the outer side of the tank wall so that the first electrical contact and the second electrical contact are protected by the protective frame. The protective frame, for example, surrounds the electrical contacts and thus permanently prevents damage thereto. The protective frame may be directly jointly provided during the production of the tank. The protective frame is therefore preferably integrally injection molded or integrally cast onto the tank. The protective frame may also form a plug socket. A cable with a corresponding connecting plug may then be connected directly to the first electrical contact and to the second electrical contact. The protective frame then also provides mechanical stability to the connection between the tank and the connecting plug.

In the method, in step b), an alternating voltage, which alternates between a positive voltage value and a negative voltage value, can be applied to the first electrical contact and to the second electrical contact. The alternating voltage is preferably rectangular. It is furthermore preferable for the alternating voltage to be symmetrical. This means that the negative voltage component and the positive voltage component correspond in form and magnitude. It is thus possible to prevent deposits from forming on one of the two contacts as a result of electrolysis.

If the tank has a heater, the method can also be expanded to include the following steps:

e.1) activating the heater if, in step d), it has been determined that frozen reducing agent is present;
e.2) deactivating the heater if, in step d), it has been determined that air is present.

If an ice cavity in the frozen reducing agent is formed around a heater in the tank, liquid reducing agent should be present in the ice cavity in order to ensure that the heat from the heater can be transported to the remaining frozen reducing agent. By contrast, air in the ice cavity constitutes a thermal insulator. If there is no connection of liquid reducing agent between the heater and the remaining frozen reducing agent in the ice cavity, further operation of the heater is generally not expedient because the heat energy output by the heater can no longer pass efficiently to the frozen reducing agent. In the case of a PTC heater (PTC: positive temperature coefficient), such a situation can be identified by monitoring the electrical current consumption of the heater. If the heater already exhibits reduced electrical current consumption shortly after activation, an ice cavity is present. In the case of a resistance heater, such a situation can be identified by determining the ratio of the current consumption to the heating voltage. If the ratio has decreased considerably, an ice cavity is present. For this reason, it is expedient for the heater to be deactivated if an insulating air layer has been detected in an ice cavity. In a further method implementation, the heater may also be operated with reduced power if air is present in the tank.

If frozen reducing agent is still present at the sensor, in the case of a corresponding embodiment of the tank, it is not important in this case whether an ice cavity filled with reducing agent or with air exists in the direct vicinity of the heater, because the second spacing between the heater and the sensor is selected in such a way that an ice cavity possibly present between the sensor and the heater is so small that adequate heat transport from the (areal) heater into the frozen reducing agent is possible despite the ice cavity. Specifically in the case of very small ice cavities, the capability of the air to transport heat from the heater to the frozen reducing agent is sufficient, so that the heater can remain activated.

The advantages and special embodiments highlighted for the method are applicable and transferable to the tank according to the invention.

With the objects of the invention in view, there is concomitantly provided a motor vehicle, comprising an internal combustion engine with an exhaust-gas treatment device which has a dosing device for reducing agent and in which the dosing device has a tank according to the invention. Furthermore, the motor vehicle can have a controller, which is set up or configured or programmed to carry out the method according to the invention.

Other features which are considered as characteristic for the invention are set forth in the appended claims, noting that the features listed individually in the claims can be combined with one another in any desired technologically expedient manner, thus highlighting further embodiments of the invention.

Although the invention is illustrated and described herein as embodied in a reducing agent tank having a sensor for determining a fill level and a motor vehicle having the tank, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE INVENTION

Figure 1:
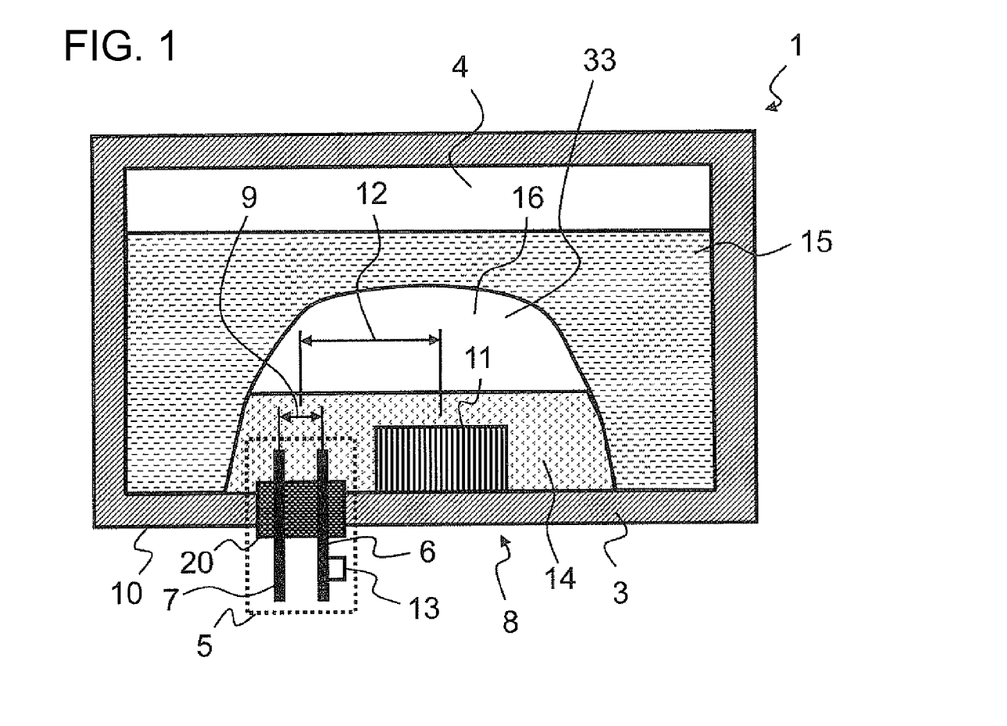
FIG. 1 is a diagrammatic, longitudinal-sectional view of a tank according to the invention for reducing agent.

Referring now in detail to the figures of the drawing for explaining the invention and the technical field in more detail by showing particularly preferred structural variants to which the invention is not restricted and noting, especially, that the figures and, in particular, the illustrated proportions are merely diagrammatic, and first, particularly, to FIG. 1 thereof, there is seen a tank 1. The tank 1 has a tank wall 3 which delimits an interior 4. An ice cavity 33 is formed in frozen reducing agent 15 which is situated in the tank 1. The ice cavity 33 is filled partially with air 16 and partially with liquid reducing agent 14 (which in this case, in particular, is a urea-water solution). The ice cavity 33 is formed around an (electrically regulable, two-dimensional) heater 11. The heater 11 is disposed on the tank wall 3 in the region of a tank base or bottom 10. A sensor 5 is situated at a second spacing 12 from the heater 11. The sensor 5 is likewise disposed in the tank wall 3, specifically in the tank base 10. The sensor 5 has a first electrical contact 6 and a second electrical contact 7.

The first electrical contact 6 and the second electrical contact 7 are disposed at a first spacing 9 from one another and are lead through the tank wall 3 of the tank 1 with a seal 20. The temperature in the interior 4 of the tank 1 or the temperature of the reducing agent can be detected from an outer side 8 of the tank 1 through the use of a temperature sensor 13 fastened to the first electrical contact 6.

Figure 2:
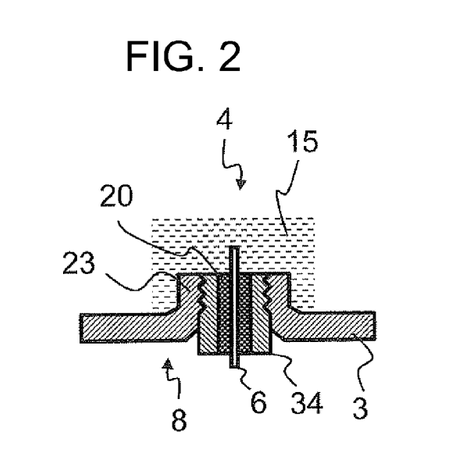
FIG. 2 is an enlarged, sectional view of a first structural variant for electrical contacts.

FIG. 2 shows an example of the way in which an electrical contact can extend through a tank wall 3. The tank wall 3 has an inwardly protruding portion 23 into which a threaded tube 34 is inserted. The first electrical contact 6 is disposed in the threaded tube 34 with a seal 20. The interior 4 of a tank which is, for example, filled with frozen reducing agent 15 is sealed off with respect to the outer side 8 through the use of the seal 20.

Figure 3:
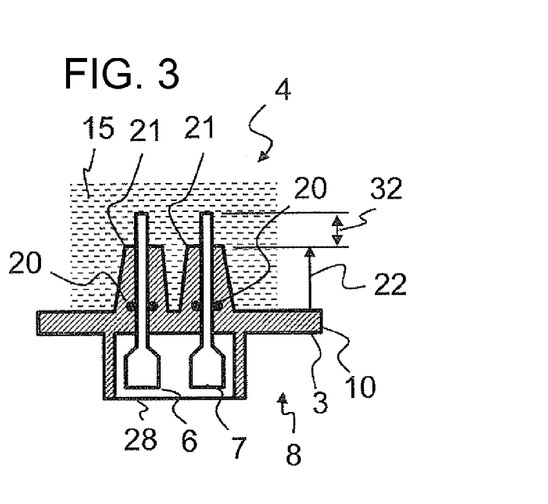
FIG. 3 is an enlarged, sectional view of a second structural variant for electrical contacts.

FIG. 3 shows a further example of the way in which a first electrical contact 6 and a second electrical contact 7 can extend through a tank wall 3. In this case, the tank wall 3 is penetrated in the region of the tank base 10. The first electrical contact 6 and the second electrical contact 7 are embedded into the tank wall 3 through the use of seals 20. The tank interior 4, which is filled with reducing agent 15, is thus sealed off with respect to an outer side 8. A protective frame 28, which is attached to the tank wall 3 on the outer side 8, protects the first electrical contact 6 and the second electrical contact 7. The protective frame 28 may be directly jointly provided during the production of the tank 1 so as to be in one piece therewith. The protective frame 28 may, for example, be integrally injection molded or integrally cast onto the tank 1. In the interior 4, a respective shoulder 21 for each of the first electrical contact 6 and the second electrical contact 7 is provided on the tank wall 3 in the region of the first electrical contact 6 and of the second electrical contact 7. The shoulders 21 serve to define a reserve level 22 in the tank (the reserve level is the fill level in the tank when only the reserve volume of liquid reducing agent is present). The first electrical contact 6 and the second electrical contact 7 each project out of the shoulders 21 over a first length 32. Reliable electrically conductive contact between the reducing agent present in the interior 4 and the first electrical contact 6 and the second electrical contact 7 is thus ensured. The configuration according to FIG. 3 is suitable, in particular, for a configuration of the sensor in the tank base 10.

Figure 4:
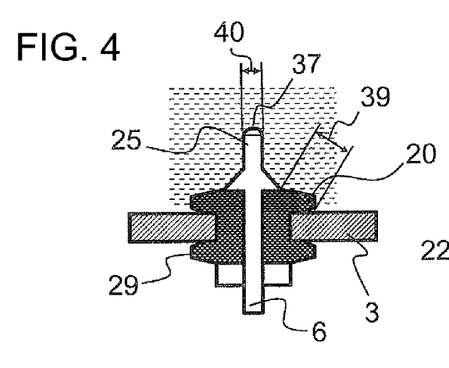
FIG. 4 is an enlarged, sectional view of a third structural variant for electrical contacts.

FIG. 4 shows a further example of the way in which an electrical contact can extend through a tank wall 3. In this case, the first electrical contact 6 is in the form of a rivet 25. The rivet 25 braces a rubber bushing 29 as a seal 20 against the tank wall 3.

Figure 5:
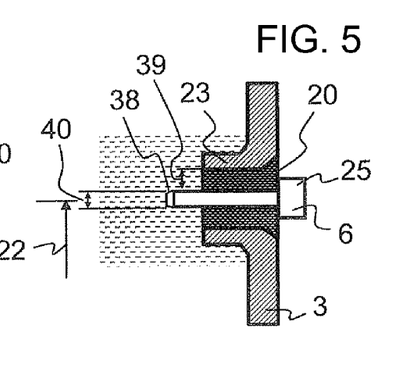
FIG. 5 is an enlarged, sectional view of a fourth structural variant for electrical contacts.

FIG. 5 shows a first electrical contact 6 which is inserted into a side region of a tank wall 3 (tank side wall). In this case, too, only the first electrical contact 6 is shown as an example. The first electrical contact 6 is likewise in the form of a rivet 25 which is inserted through the use of a seal 20 into an inwardly protruding portion 23 of the tank wall 3. A reserve level 22 is defined in this case by the configuration of the first electrical contact 6 in the tank wall 3 and not by the height of a shoulder 21. The further that the tank base is positioned from the first electrical contact 6 or the electrical contacts on the tank wall 3, the higher the reserve level 22.

FIGS. 4 and 5 furthermore illustrate particularly preferred shapes of a first electrical contact 6. The shapes are selected in such a way that no deposits and/or accumulations of reducing agent and/or reducing agent residues can occur in or on the first electrical contact 6, or that such deposits and/or accumulations are avoided to the greatest possible extent. Such deposits may lead to a short circuit between the first electrical contact 6 and the tank wall 3 and/or a short circuit between the first electrical contact 6 and the second electrical contact 7. In particular, the end of the first electrical contact 6 may have a correspondingly suitable construction in this case. FIG. 4 shows, for example, a lens shape 37 for the end of the first electrical contact 6. FIG. 5 shows a first electrical contact 6 which has a preferably encircling bevel 38 on the end thereof. The thickness 40 of the first electrical contact 6 may also be selected appropriately. The thickness 40 is preferably at least 0.5 mm [millimeters], preferably at least 1 mm and particularly preferably at least 2 mm.

Furthermore, in order to prevent a short circuit as a result of deposits and/or accumulations, it is important for the insulation of the first electrical contact 6 with respect to the tank wall 3 and with respect to a second electrical contact 7 to have an adequate width 39. A width 39 preferably means a shortest distance on the surface of the insulation from the tank wall 3 to the first electrical contact 6. In FIG. 4 and FIG. 5, the insulation is formed by the seal 20. The width 39 is preferably at least 0.5 mm [millimeters] and particularly preferably at least 1 mm.

These special embodiments proposed for the first electrical contact 6 are analogously transferable to a second electrical contact 7, which is however not separately illustrated in FIG. 4 and FIG. 5 for the sake of simplicity.

Figure 6:
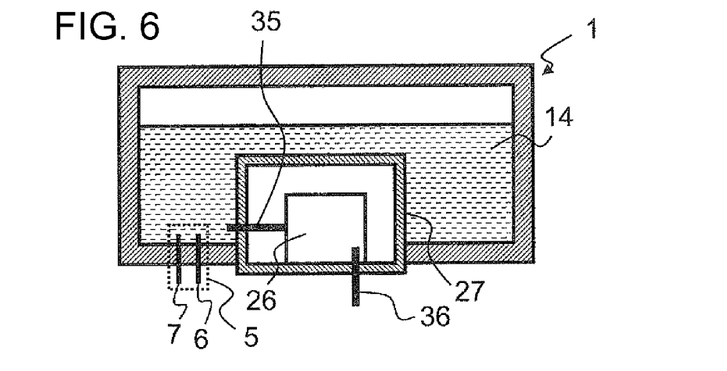
FIG. 6 is a longitudinal-sectional view of a tank having a temperature sensor.

FIG. 6 shows a further tank 1 according to the invention with a sensor 5 which is formed with a first electrical contact 6 and a second electrical contact 7. The tank 1 has a metallic pot 27 in which a delivery unit 26 for transporting and/or dosing the reducing agent is disposed. Through the use of the delivery unit 26, the liquid reducing agent 14 can be discharged from the interior of the tank 1 through an extraction point 35. The delivery unit 26 may include, as parts, for example, a filter, a pump, a valve, transport lines, etc. which are jointly integrated in the metallic pot 27. The liquid reducing agent is supplied (if appropriate at elevated pressure) through an outlet line 36 from the delivery unit 26, for example, to a non-illustrated dispensing point or dosing point of an exhaust system.

Figure 7:
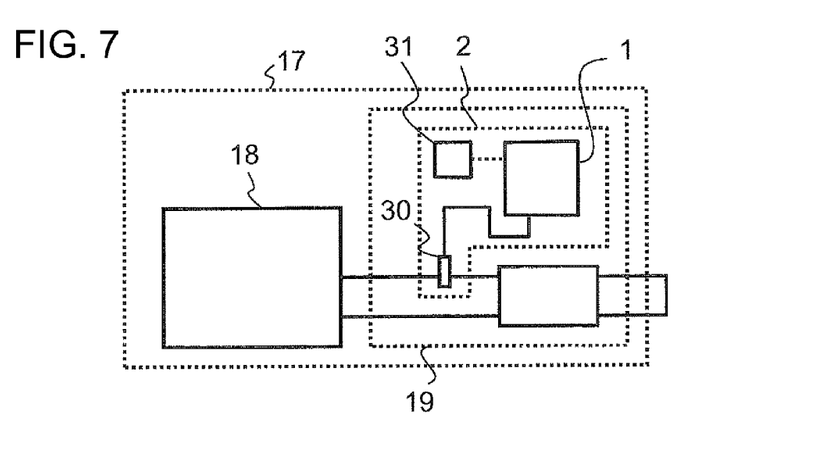
FIG. 7 is a longitudinal-sectional view of a motor vehicle having a tank.

FIG. 7 shows a motor vehicle 17 having an internal combustion engine 18 and an exhaust-gas treatment device 19. A dosing device 2, which has a tank 1, is provided in the exhaust-gas treatment device 19. Liquid reducing agent stored in the tank 1 can be dosed in predefined quantities through an injector 30 by using a delivery unit (which is preferably integrated in the tank) of the exhaust-gas treatment device 19. Fill level signals determined by the individual sensors may be evaluated in a suitable controller 31 in order to obtain a corrected fill level signal.

Figure 8:
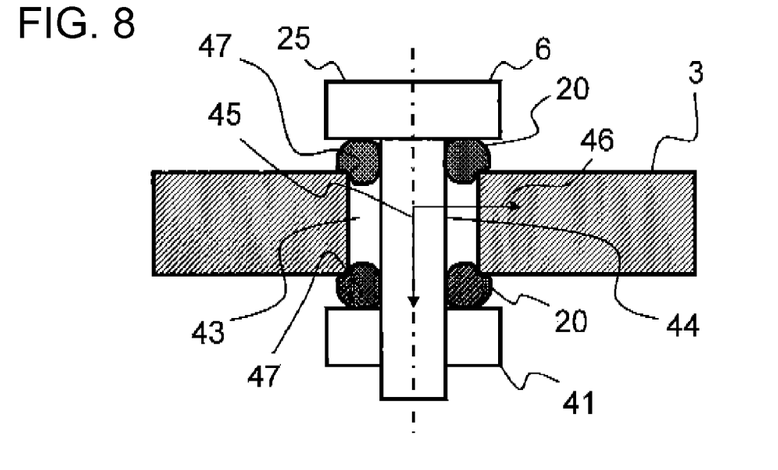
FIG. 8 is a further enlarged, sectional view of a fifth structural variant for electrical contacts.

FIG. 8 shows a structural variant of a first electrical contact 6. This structural variant is also transferable to a second electrical contact. The first electrical contact 6 is in the form of a rivet 25 which is guided through the tank wall 3. The rivet 25 extends through an opening 43 in the tank wall 3. The cross-sectional area of the opening 43 is larger than the cross-sectional area 44 of the rivet 25, so that a gap is formed between the rivet 25 and the tank wall 3. It is preferable for the rivet 25 and the opening 43 to have a rotationally symmetrical form or shape. The width of the gap and/or the size of the opening 43 and the cross-sectional area 44 of the rivet 25 are preferably selected in such a way that two O-rings 20 are braced in each case both in an axial direction 45 as well as in a radial direction 46 by the rivet 25 and by the tank wall 3. This may be achieved by virtue of the O-rings 20 being braced in each case against an edge 47 of the opening 43 by the rivet 25. An inexpensive fluid-tight leadthrough of a first electrical contact 6 and/or of a second electrical contact through the tank wall 3 can be produced in this way.

Figure 9:
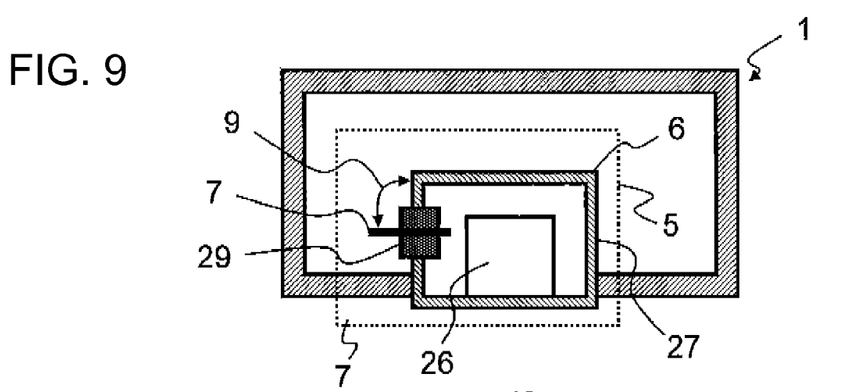
FIG. 9 is a longitudinal-sectional view of a tank with a sixth structural variant for electrical contacts.

FIG. 9 shows a sixth structural variant of a first electrical contact 6 and of a second electrical contact 7 for a tank 1 according to the invention with a sensor 5. A metallic pot 27 is inserted into the tank 1. A delivery unit 26 for delivering reducing agent is disposed in the metallic pot 27. The metallic pot 27 forms the first electrical contact 6 of the sensor 5. The second electrical contact 7 is additionally provided. In this structural variant, the second electrical contact 7 extends through the metallic pot 27 and the second electrical contact is sealed off with respect to the metallic pot 27 through the use of a seal element. The seal element is, in the present case, in the form of a rubber bushing 29. Other structural variants of the seal element can, however, also be used. In a modified structural variant, the second electrical contact 7 may also extend through the tank wall 3 separately from the metallic pot 27. For example, the second electrical contact 7 may be disposed in the tank wall adjacent the metallic pot 27. The first electrical contact 6, which is in the form of a metallic pot 27, and the second electrical contact 7, preferably have a first spacing 9 of less than 5 cm [centimeters] from one another.

Figure 10:
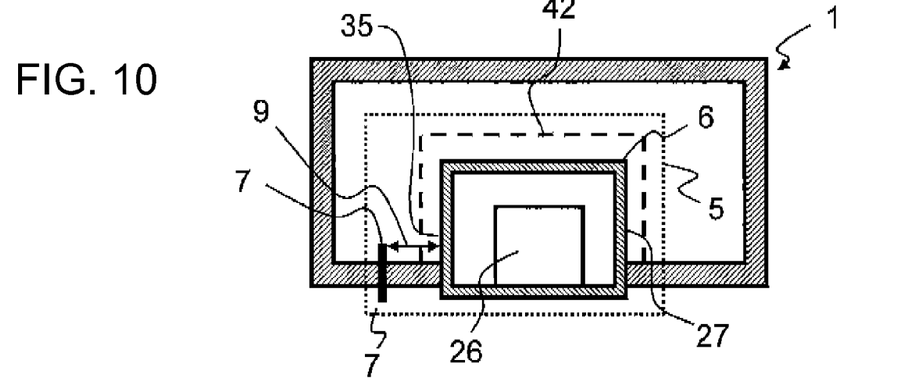
FIG. 10 is a longitudinal-sectional view of a tank with a seventh structural variant for electrical contacts.

FIG. 10 shows a seventh structural variant for a first electrical contact 6 and for a second electrical contact 7 for a tank 1 according to the invention with a sensor 5. A metallic pot 27 with a delivery unit 26 is likewise inserted into the tank 1 shown herein. In this case, too, the metallic pot 27 forms the first electrical contact 6. A filter 42 is disposed around the metallic pot 27. An extraction point 35 for reducing agent, through which reducing agent is transported from the tank 1 to the delivery unit 26, is disposed on the metallic pot 27. Reducing agent which passes from the tank 1 to the extraction point 35 is filtered by the filter 42. The second electrical contact 7 is disposed adjacent the metallic pot 27 with the filter 42. In this case, too, there is a spacing 9 of less than 5 cm [centimeters] between the first electrical contact 6 and the second electrical contact 7. The filter 42 is disposed between the first electrical contact 6 and the second electrical contact 7. This is, however, not disadvantageous for the measurement of the electrical properties of the reducing agent between the first electrical contact 6 and the second electrical contact 7.

The exemplary embodiments of electrical contacts illustrated in FIGS. 2 to 5 and 8 are not only suitable for electrical contacts which extend through the tank wall. The exemplary embodiments may also be transferred to electrical contacts which extend through a possibly metallic pot in the tank wall, in which a delivery unit may be disposed in the metallic pot. Such a configuration of an electrical contact is illustrated, for example, in FIG. 9.

A reducing agent tank with a particularly advantageous fill level sensor and a particularly advantageous method for operating a reducing agent tank with a fill level determining device have thus been specified herein.

The invention claimed is:
1. A tank for a reducing agent, the tank comprising:
  a tank wall having an outer side;
  an interior at least partially delimited by said tank wall; and
  a sensor disposed at said tank wall and having a first electrical contact and a second electrical contact;
  a temperature sensor attached at least to one of said electrical contacts at said outer side of said tank wall;
  said first electrical contact and said second electrical contact communicating in an electrically conductive manner with said interior, extending through said tank wall from said interior to said outer side of said tank wall and being disposed at a first spacing of less than 5 cm from one another.

2. The tank according to claim 1, wherein at least one of said first electrical contact or said second electrical contact is formed by a metallic pot disposed in the tank.

3. The tank according to claim 2, wherein one of said electrical contacts is formed by said metallic pot and the other of said electrical contacts extends through said metallic pot.

4. A tank for a reducing agent, the tank comprising:
- a tank wall having an outer side;
- an interior at least partially delimited by said tank wall;
- a sensor disposed at said tank wall and having a first electrical contact and a second electrical contact, at least one of said first electrical contact or said second electrical contact being formed by a metallic pot disposed in the tank; and
- a filter surrounding said metallic pot, one of said electrical contacts being formed by said metallic pot and the other of said electrical contacts being disposed outside said filter;
- said first electrical contact and said second electrical contact communicating in an electrically conductive manner with said interior, extending through said tank wall from said interior to said outer side of said tank wall and being disposed at a first spacing of less than 5 cm from one another.

5. The tank according to claim 1, which further comprises a tank base at which said sensor is disposed.

6. A tank for a reducing agent, the tank comprising:
- a tank wall having an outer side;
- an interior at least partially delimited by said tank wall;
- a sensor disposed at said tank wall and having a first electrical contact and a second electrical contact;
- a tank base at which said sensor is disposed; and
- said first electrical contact and said second electrical contact communicating in an electrically conductive manner with said interior, extending through said tank wall from said interior to said outer side of said tank wall and being disposed at a first spacing of less than 5 cm from one another;
- at least one of said first electrical contact or said second electrical contact project from said tank base into said tank interior over a first length of at most 5 cm.

7. The tank according to claim 6, which further comprises a heater disposed at a second spacing of less than 50 cm from said sensor.

8. The tank according to claim 6, which further comprises a temperature sensor attached at least to one of said electrical contacts at said outer side of said tank wall.

9. The tank according to claim 1, which further comprises an integrally injection molded or integrally cast protective frame at said outer side of said tank wall configured to protect said first electrical contact and said second electrical contact.

10. A motor vehicle, comprising:
- an internal combustion engine; and
- an exhaust-gas treatment device associated with said internal combustion engine and having a dosing device for reducing agent;
- said dosing device having a tank including:
  - a tank wall having an outer side;
  - an interior at least partially delimited by said tank wall; and
  - a sensor disposed at said tank wall and having a first electrical contact and a second electrical contact;
  - a temperature sensor attached at least to one of said electrical contacts at said outer side of said tank wall;
  - said first electrical contact and said second electrical contact communicating in an electrically conductive manner with said interior, extending through said tank wall from said interior to said outer side of said tank wall and being disposed at a first spacing of less than 5 cm from one another.

* * * * *